(12) United States Patent
Zhang et al.

(10) Patent No.: US 11,149,005 B2
(45) Date of Patent: Oct. 19, 2021

(54) ORGANIC AMINE ESTER DERIVATIVE DRUG OF 2-(α-HYDROXYPENTYL)BENZOIC ACID

(71) Applicant: YAOPHARMA CO., LTD., Chongqing (CN)

(72) Inventors: Ling Zhang, Sichuan (CN); Zhirong Zhang, Sichuan (CN); Jianbo Li, Henan (CN)

(73) Assignee: YAOPHARMA CO., LTD., Chongqing (CN)

( * ) Notice: Subject to any disclaimer, the term of this patent is extended or adjusted under 35 U.S.C. 154(b) by 0 days.

(21) Appl. No.: 16/979,001

(22) PCT Filed: Apr. 28, 2019

(86) PCT No.: PCT/CN2019/084830
§ 371 (c)(1),
(2) Date: Sep. 8, 2020

(87) PCT Pub. No.: WO2019/218864
PCT Pub. Date: Nov. 21, 2019

(65) Prior Publication Data
US 2021/0002224 A1    Jan. 7, 2021

(30) Foreign Application Priority Data

May 17, 2018 (CN) .......................... 201810474269.1

(51) Int. Cl.
*C07D 211/14* (2006.01)
*C07C 229/38* (2006.01)

(52) U.S. Cl.
CPC .......... *C07D 211/14* (2013.01); *C07C 229/38* (2013.01)

(58) Field of Classification Search
CPC .............................. C07D 211/14; C07C 229/38
See application file for complete search history.

(56) References Cited

FOREIGN PATENT DOCUMENTS

| CN | 101822841 A |   | 9/2010 |
| CN | 102225940 A |   | 10/2011 |
| CN | 101822841 B |   | 2/2012 |
| CN | 103127025 A | * | 6/2013 |
| CN | 104546828 A |   | 4/2015 |
| CN | 104628649 A |   | 5/2015 |
| CN | 106800537 A |   | 6/2017 |
| CN | 106928155 A |   | 7/2017 |
| CN | 108715579 A |   | 10/2018 |

OTHER PUBLICATIONS

CN 103127025, English Translation of Abstract and SciFinder search result summary, Jun. 2013 (Year: 2013).*
ISR for PCT/CN2019/084830 dated Jul. 30, 2019, 7 pages.
Written Opinion for PCT/CN2019/084830 dated Jul. 30, 2019, 10 pages.

Li et al., Synthesis and evaluation of nitric oxide-releasing derivatives of 3-n-butylphthalide as anti-platelet agents, Bioorganic & Medicinal Chemistry Letters 21, 2011, pp. 4210-4214.
Min et al., One-pot synthesis of 2-(1-acyloxypentyl) benzoic acids, Chinese Chemical Letters 19, 2008, pp. 915-917.
Sheng, X., et al., Novel hybrids of 3-n-butylphthalide and edaravone: Design, synthesis and evaluations as potential anti-ischemic stroke agents; Bioorganic & Medical Chemistry Letters; 2015, vol. 25, pp. 3535-3540, Elsevier.
Extended European Search Report for EP Application No. 19803484.5, dated May 4, 2021, 7 pages.
Hua Kai, et al., The edaravone and 3-n-butylphthalide ring-opening derivative 10b effectively attenuates cerebral ischemia injury in rats; Acta Pharmacologica Sinica; 2015, vol. 36, pp. 917-927.
Wang Xiaoli, et al., Novel Hybrids of Optically Active Ring-Opened 3-n-Butylphthalide Derivative and Isosorbide as Potential Anti-Ischemic Stroke Agents; Journal of Medicinal Chemistry; Mar. 19, 2013, vol. 56, pp. 3078-3089.
Zhang Chao, et al., (S)-ZJM-289 Preconditioning Induces a Late Phase Protection Against Nervous Injury Induced by Transient Cerebral Ischemia and Oxygen-Glucose Deprivation; Neurotoxicity Research; 2014, vol. 26, pp. 16-31.

(Continued)

*Primary Examiner* — Kortney L. Klinkel
*Assistant Examiner* — William Y Lee
(74) *Attorney, Agent, or Firm* — Nixon Peabody LLP; Jeffrey L. Costellia (57) ABSTRACT

An organic amine ester derivative drug of 2-(α-hydroxypentyl)benzoic acid and a preparation method thereof and an use thereof are disclosed. The present disclosure particularly relates to a compound having the general formula I or a pharmaceutically acceptable salt thereof, and a pharmaceutically acceptable formulation prepared from the compound or the pharmaceutically acceptable salt thereof. The compound having the general formula I or the pharmaceutically acceptable salt thereof has in vitro a good solubility and a low hygroscopicity, and has in vivo a bioavailability and a brain aggregation concentration that are significantly greater than those of the original medicine butyphthalide and/or an improving drug efficacy. The use of the compound in the preparation of a drug for preventing and/or treating heart and cerebral ischemic diseases, a drug for preventing and/or treating heart and cerebral artery occlusion diseases, an anti-parkinsonian drug and an anti-senile-dementia drug is also disclosed.

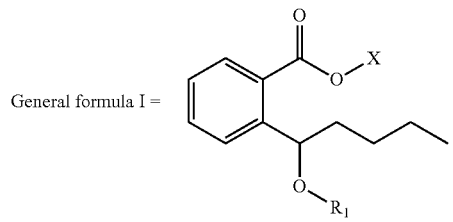

General formula I =

20 Claims, 3 Drawing Sheets

(56) References Cited

OTHER PUBLICATIONS

Wang Xiao-Li, et al., Synthesis and biological evaluation of nitric oxide (NO)-hydrogen sulfide (H2S) releasing derivatives of (S)-3-butylphthalide as potential antiplatelet agents; Chinese Journal of Natural Medicines; 2016, vol. 14, pp. 946-953.

Wang Xiaoli, et al., Design, synthesis and biological evaluation of hydrogen sulfide releasing derivatives of 3-n-butylphthalide as potential antiplatelet and antithrombotic agents; Organic and Biomolecular Chemistry; Aug. 21, 2014, vol. 12, No. 31, pp. 5995-6004.

\* cited by examiner

ORGANIC AMINE ESTER DERIVATIVE DRUG OF 2-(α-HYDROXYPENTYL)BENZOIC ACID

CROSS-REFERENCE TO RELATED APPLICATIONS

This application is the National Phase of International Application PCT/CN2019/084830, filed Apr. 28, 2019, which designated the United States. This application also includes a claim of priority under 35 U.S.C. § 119(a) and § 365(b) to Chinese Application No. 201810474269.1 filed May 17, 2018, the entirety of which is hereby incorporated by reference.

TECHNICAL FIELD

The present disclosure relates to the field of medicines, and more particularly relates to a drug of an organic amine ester derivative of 2-(α-hydroxypentyl)benzoic acid that has a good solubility, a low hygroscopicity, a simple formulation preparing process and a high bioavailability and can improve the brain aggregation concentration, and the use thereof in the preparation of a drug for preventing and/or treating heart and cerebral ischemic diseases, a drug for preventing and/or treating heart and cerebral artery occlusion diseases, an anti-parkinsonian drug and an anti-senile-dementia drug.

BACKGROUND

Butyphthalide, with the chemical name of dl-3-n-butylphthalide (NBP, 1), is extracted from the seed of *Apium graveolens*, a natural edible plant, and is a novel drug for preventing and treating ischemic stroke, which China independently develops and owns the intellectual property right, with the trade name of NBP. Pharmacodynamic studies indicate that Dl-NBP acts on multiple pathological phases of the brain damage caused by ischemic stroke, and has a strong effect of resisting cerebral ischemia. The medicine was approved by the National Medical Products Administration in 2002 to be used to treat cardiovascular diseases such as mild and moderate acute ischemic stroke. Experimental studies in recent years have found that NBP cannot only resist the brain damage caused by ischemia, but also presents the effect of protection with respect to other damages on the nervous system such as neurodegenerative diseases. However, NBP has a poor water solubility, and is a pale-yellow oily liquid at room temperature. Liquid drugs have more complicated processes of formulation preparing than those of solid drugs. Currently, the dosage forms of butyphthalide are butyphthalide softgel and butyphthalide sodium-chloride injection. Softgels have a high production cost and a complicated production process. Furthermore, the oral bioavailability is low, and the half life is short. As for the clinical effect of butyphthalide, slight rising of the amounts of aspartate transaminase and alanine aminotransferase appears, and adverse reactions such as abdominal discomfort, nausea, rash and mental symptoms occasionally happen. All of the above restrain the application and the efficacy of NBP.

A prodrug is obtained by modifying the chemical structure of the molecule of a medicine that originally has a bioactivity but has certain deficiencies by connecting the molecule to one or more modifying carrier groups, to make it become a compound having in vitro no bioactivity or a reduced bioactivity. In vivo, especially under an enzymatic action or non-enzymatic action at the site of action, the modifying group of the prodrug is removed, and it is recovered into the original medicine to provide the efficacy. A prodrug can facilitate to overcome the defects of many active medicines, such as increasing the lipo-hydro partition coefficient of a medicine, improving the targeting ability and the stability of a medicine, reducing the toxicity and side effect of a medicine and so on.

The Chinese patent CN1243541C discloses a 2-(α-hydroxypentyl)benzoic acid salt as a novel drug that has obvious effects of resisting platelet aggregation and improving microcirculation, and has pharmaceutical activity on myocardial and cerebral ischemia and myocardial and cerebral artery occlusion, and its potassium salt, potassium 2-(α-hydroxypentyl)benzoate (dl-PHPB), as a butyphthalide prodrug, has a greatly improved water solubility. Numerous studies indicate that Dl-PHPB can be rapidly converted into butyphthalide in organism, and its efficacy is equal to or better than that of an equal amount of butyphthalide. The Chinese patent CN104086399B discloses a sodium salt of 5-bromo-2-(α-hydroxypentyl)benzoic acid for treating cerebrovascular diseases. The results of animal-model studies indicate that the compound has the effect of protection with respect to the reperfusion injury of cerebral ischemia, can ameliorate dyskinesia, reduce volume of cerebral infarction, and alleviate encephaledema, and is effective when administered after ischemia. Furthermore, the compound, as a prodrug of a butyphthalide derivative, has a greatly improved water solubility.

However, the potassium salts and the sodium salts of 2-(α-hydroxypentyl)benzoic acid and its derivatives have a high hygroscopicity and a poor stability (ring closing easily happens), and therefore the process of preparing the formulations has high requirements on the environment and the pH value, which greatly increases the production cost. Currently, there has not been a derivative of 2-(α-hydroxypentyl)benzoic acid that can overcome those disadvantages. Therefore, it is very necessary to develop a derivative of 2-(α-hydroxypentyl)benzoic acid that has a good solubility and a low hygroscopicity, can be easily prepared into a solid formulation to reduce the production cost, has a bioavailability significantly greater than that of the original medicine, and can quickly degrade in vivo into the original medicine and improve the brain aggregation concentration.

SUMMARY

In view of the disadvantages of the prior art, an object of the present disclosure is to provide a novel organic amine ester derivative of 2-(α-hydroxypentyl)benzoic acid having the structure of the general formula I for treating brain diseases, and a preparation method and a use thereof. The present disclosure has found by inventive studies that the organic amine ester derivative of 2-(α-hydroxypentyl)benzoic acid according to the present disclosure greatly improves the solubility of the drug in solutions, has a low hygroscopicity, has an oral bioavailability significantly greater than the original medicine butyphthalide, greatly improves the aggregation concentration in the brain of butyphthalide, and prolongs its duration of aggregation in the brain, thereby having a good druggability and a superior clinical application value.

The first object of the present disclosure is to provide a novel organic amine ester derivative of 2-(α-hydroxypentyl)benzoic acid having the structure of the general formula I for treating brain diseases, and a preparation method thereof.

In order to achieve the above objects, the present disclosure employs the following technical solutions:

The present disclosure provides a drug of an organic amine ester derivative having the general formula I or a pharmaceutically acceptable salt thereof, General formula I =

$R_1$ represents hydrogen atom or C1-C10 alkyl that contains acyl or acyloxy; and X is wherein $R_2$ is C1-C10 alkylene or C3-C7 cycloalkylene, and $R_3$ and $R_4$ are independently selected from hydrogen atom, C1-C10 alkyl and C3-C7 cycloalkyl; or X is wherein n=0-10, and $R_5$ is a 5-15-membered heterocycle or substituted heterocycle containing 1-2 N atoms.

Preferably, the present disclosure provides the organic amine ester derivative of 2-(α-hydroxypentyl)benzoic acid or a pharmaceutically acceptable salt thereof, wherein X is wherein $R_2$ is C1-C10 alkylene or C3-C7 cycloalkylene, and $R_3$ and $R_4$ are independently selected from hydrogen atom, C1-C10 alkyl and C3-C7 cycloalkyl; or X is wherein n=2, and $R_6$ is selected from

More preferably, the present disclosure provides a method for preparing a drug of the organic amine ester derivative of 2-(α-hydroxypentyl)benzoic acid, wherein the method comprises firstly performing ring opening to butyphthalide, then performing a reaction with acetyl chloride, and finally performing acylation with X—OH to form the ester, wherein the reaction equation is as follows:

wherein X is wherein $R_2$ is C1-C10 alkylene or C3-C7 cycloalkylene, and $R_3$ and $R_4$ are independently selected from hydrogen atom, C1-C10 alkyl and C3-C7 cycloalkyl; or X is wherein n=2, and $R_6$ is selected from -continued More preferably, the method comprises performing ring opening to butyphthalide in a basic condition, and then performing sequentially acidification, acetylation, and, respectively, condensation with N,N-dimethylethanolamine and 1-(2-ethoxy)piperidine to obtain ester, to obtain compounds DB-1 and DB-2.

The structural formulas of the compounds DB-1 and DB-2 are as follows:

DB-1

DB-2

The methods for synthesizing the compounds DB-1 and DB-2 are briefly described below:

(1) The Synthesis of 2-(1-acetoxylpentyl)benzoic Acid 4

Butyphthalide 1 is dissolved into methanol, added a proper amount of a solution of sodium hydroxide, and heated for reaction for 1 h. The methanol is removed by reduced-pressure evaporation, distilled water is added for diluting, and diluted hydrochloric acid is added for acidification. The water layer is extracted by using ethyl ether, the ethyl-ether layers are combined, and the ethyl-ether layer is then sequentially added triethylamine and 4-dimethylaminopyridine (DMAP), added dropwisely acetyl chloride, and stirred for reaction for 5 h. Water is added for extraction, and the organic layer is separated, and condensed to obtain a wax-like solid. The solid is recrystallized in n-hexane to obtain a white needle-like crystal.

(2) The Synthesis of the Compound DB-1

The compound 4 is weighed, added dichloromethane, HATU and the compound 5, and stirred for reaction overnight. Water is added for extraction three times, and column purification is performed, to obtain a white solid. An anhydrous ethanol-HCl solution is added to form a salt, and ethyl ether is added to form a white precipitate. The white precipitate is filtered and dried, to obtain the product of the hydrochloride of the compound DB-1.

(3) The Synthesis of the Compound DB-2

The compound 4 is weighed, added dichloromethane, HATU and the compound 6, and stirred for reaction overnight. Water is added for extraction three times, and column purification is performed, to obtain a white solid. An anhydrous ethanol-HCl solution is added to form a salt, and ethyl ether is added to form a white precipitate. The white precipitate is filtered and dried, to obtain the product of the hydrochloride of the compound DB-2.

The compounds 5 and 6 are commonly used chemical raw materials, and are commercially available.

The second object of the present disclosure is the use of the organic amine ester derivative of 2-(α-hydroxypentyl) benzoic acid according to the present disclosure or a pharmaceutically acceptable salt thereof and a formulation thereof in the preparation of a drug for preventing or treating brain diseases. The brain diseases include heart and cerebral ischemic diseases, heart and cerebral artery occlusion diseases, Parkinson's disease and senile dementia.

In order to study the improvement on the druggability of the organic amine ester derivative of 2-(α-hydroxypentyl) benzoic acid or the pharmaceutically acceptable salt thereof according to the present disclosure, the investigation on the in-vitro physicochemical property and the preliminary experiments on the in-vivo distribution with respect to the above compounds are performed. The experimental results indicate that the present disclosure greatly improves the solubility of the drug in solutions, has a low hygroscopicity, has an oral bioavailability significantly greater than the original medicine butyphthalide, greatly improves the aggregation concentration in the brain of butyphthalide, and prolongs its duration of aggregation in the brain, to simplify the production process, reduce the production cost, improve the efficacy, reduce the administration dosage, reduce toxicity and side effect, and further improve the effectiveness and safety of the product.

Therefore, the present disclosure provides an organic amine ester derivative of 2-(α-hydroxypentyl)benzoic acid, wherein the organic amine ester derivative of 2-(α-hydroxypentyl)benzoic acid is a compound having the following general formula I, or the organic amine ester derivative of 2-(α-hydroxypentyl)benzoic acid is a pharmaceutically acceptable salt formed by a compound having the following general formula I and an inorganic acid or organic acid:

wherein, in the general formula I, $R_1$ represents hydrogen atom or C1-C10 alkyl, wherein the C1-C10 alkyl contains acyl or acyloxy; and X represents a substituent wherein $R_2$ is C1-C10 alkylene or C3-C7 cycloalkylene, and $R_3$ and $R_4$ are independently selected from hydrogen atom, C1-C10 alkyl and C3-C7 cycloalkyl; or,

X represents a substituent wherein n is an integer selected from an interval [0, 10] and $R_5$ represents a 5-15-membered heterocycle or substituted heterocycle containing one or two nitrogen atoms.

In an embodiment, the organic amine ester derivative of 2-(α-hydroxypentyl)benzoic acid is a compound having the following general formula II, or the organic amine ester derivative of 2-(α-hydroxypentyl)benzoic acid is a pharmaceutically acceptable salt formed by a compound having the following general formula II and an inorganic acid or organic acid;

(II)

wherein $R_1$ is ethyl that contains acyl; and
X represents a substituent wherein $R_2$ is C1-C10 alkylene or C3-C7 cycloalkylene, and $R_3$ and $R_4$ are independently selected from hydrogen atom, C1-C10 alkyl and C3-C7 cycloalkyl; or, X represents a substituent wherein n=2 and $R_5$ represents any one of

In an embodiment, the organic amine ester derivative of 2-(α-hydroxypentyl)benzoic acid is a compound having the following structure, or the organic amine ester derivative of 2-(α-hydroxypentyl)benzoic acid is a pharmaceutically acceptable salt formed by a compound having the following structure and an inorganic acid or organic acid:

DB-1 wherein $R_1$ is ethyl that contains acyl; and
X represents a substituent wherein $R_2$ is ethylidene, $R_3$ is methyl and $R_4$ is methyl.

In an embodiment, the organic amine ester derivative of 2-(α-hydroxypentyl)benzoic acid is a compound having the following structure, or the organic amine ester derivative of 2-(α-hydroxypentyl)benzoic acid is a pharmaceutically acceptable salt formed by a compound having the following structure and an inorganic acid or organic acid:

DB-2 wherein $R_1$ is ethyl that contains acyl; and
X represents a substituent wherein n=2 and $R_5$ represents

In an embodiment, the inorganic acid comprises any one of hydrochloric acid, hydrobromic acid, sulfuric acid and phosphoric acid; and the organic acid comprises any one of acetic acid, trifluoroacetic acid, lactic acid, pyruvic acid, propanedioic acid, succinic acid, glutaric acid, fumaric acid, tartaric acid, maleic acid, citric acid, ascorbic acid, oxalic acid, camphoric acid, gluconic acid, glucuronic acid, pamoic acid, methanesulfonic acid, ethanesulfonic acid, aminosulfonic acid and p-toluenesulfonic acid.

An embodiment of the present disclosure further provides a method for preparing the organic amine ester derivative of 2-(α-hydroxypentyl)benzoic acid stated above, the method for preparing the compound having the general formula I comprises:

performing an acylation reaction between a compound 2-(α-hydroxypentyl)benzoic acid having the following structure 1 and an acylating reagent having the following general formula III, to obtain an intermediate compound having the following general formula IV; and performing an esterification reaction between the intermediate compound and an esterifying reagent having the following general formula V, to obtain the compound having the general formula I;

I

III

IV

X—OH;

V wherein $R_1$ in the general formula III of the acylating reagent represents hydrogen atom or C1-C10 alkyl, wherein the C1-C10 alkyl contains acyl or acyloxy; and X in the general formula V of the esterifying reagent represents a substituent wherein $R_2$ is C1-C10 alkylene or C3-C7 cycloalkylene, and $R_3$ and $R_4$ are independently selected from hydrogen atom, C1-C10 alkyl and C3-C7 cycloalkyl; or,

X represents a substituent wherein n is an integer selected from an interval [0, 10] and $R_5$ represents a 5-15-membered heterocycle or substituted heterocycle containing one or two nitrogen atoms.

In an embodiment, $R_1$ in the general formula III of the acylating reagent is acetyl; and X in the general formula V of the esterifying reagent represents a substituent wherein $R_2$ is C1-C10 alkylene or C3-C7 cycloalkylene, and $R_3$ and $R_4$ are independently selected from hydrogen atom, C1-C10 alkyl and C3-C7 cycloalkyl; or,

X represents a substituent wherein n=2 and $R_5$ represents any one of

In an embodiment, the esterifying reagent is N,N-dimethylethanolamine, which means that X in the general formula V of the esterifying reagent represents a substituent wherein $R_2$ is ethylidene, $R_3$ is methyl and $R_4$ is methyl; and the step of performing an esterification reaction between the intermediate compound and an esterifying reagent having the following general formula V, to obtain the compound having the general formula I comprises:

performing an esterification reaction between the intermediate compound and N,N-dimethylethanolamine, to obtain the compound having the following structure;

DB-1

In an embodiment, the esterifying reagent is 1-(2-ethoxy) piperidine, which means that X in the general formula V of the esterifying reagent represents a substituent wherein n=2 and $R_5$ represents and the step of performing an esterification reaction between the intermediate compound and an esterifying reagent having the following general formula V, to obtain the compound having the general formula I comprises:

performing an esterification reaction between the intermediate compound and 1-(2-ethoxy)piperidine, to obtain the compound having the following structure;

DB-2

In an embodiment, the method further comprises:

preparation of the salt: adding the inorganic acid or organic acid into the obtained compound having the general formula I to perform the reaction, to obtain the pharmaceutically acceptable salt formed by the compound having the general formula I and the inorganic acid or organic acid.

In an embodiment, the inorganic acid comprises any one of hydrochloric acid, hydrobromic acid, sulfuric acid and phosphoric acid; and the organic acid comprises any one of acetic acid, trifluoroacetic acid, lactic acid, pyruvic acid, propanedioic acid, succinic acid, glutaric acid, fumaric acid, tartaric acid, maleic acid, citric acid, ascorbic acid, oxalic acid, camphoric acid, gluconic acid, glucuronic acid, pamoic acid, methanesulfonic acid, ethanesulfonic acid, aminosulfonic acid and p-toluenesulfonic acid.

An embodiment of the present disclosure further provides a pharmaceutically acceptable formulation prepared from the organic amine ester derivative of 2-(α-hydroxypentyl) benzoic acid stated above, wherein the formulation comprises any one of a solid formulation, a semi-solid formulation and a liquid formulation.

In an embodiment, the solid formulation comprises any one of a common tablet, a dispersible tablet, a sustained release tablet, a soft capsule, a hard capsule, a granula, a pulvis or a suppository;

the semi-solid formulation comprises any one of an ointment, a paste and a gel; and the liquid formulation comprises any one of an injection, a drop, a solution, an emulsion and a suspension.

In an embodiment, the formulation is applied to prepare a drug for preventing and/or treating heart and cerebral ischemic diseases, a drug for preventing and/or treating heart and cerebral artery occlusion diseases, an anti-parkinsonian drug and an anti-senile-dementia drug.

As compared with the prior art, the technical solutions of the present disclosure have prominent substantive features and represent notable progress, which is particularly expressed as follows:

1) The inventors inventively modify 2-(α-hydroxypentyl) benzoic acid with the organic amines. Organic amines are modifying groups that are feasible and can obviously improve the druggability. Firstly, the organic amines have functional groups that the medicine can be connected to. Secondly, the organic amine ester derivative of 2-(α-hydroxypentyl)benzoic acid is degradable in vivo, to release 2-(α-hydroxypentyl)benzoic acid, which is converted into butyphthalide to serve as a medicine. Thirdly, the linking approach is simple, can be easily adapted for large-scale production, and has a low production cost, thereby providing a good application prospect. What is the most important is that the organic-amine derivative has no obvious toxicity and side effect.

2) As compared with the original medicine butyphthalide, the organic amine ester derivative of 2-(α-hydroxypentyl) benzoic acid or the pharmaceutically acceptable salt thereof has in vitro a good solubility and a low hygroscopicity, which greatly improves the druggability.

3) As compared with the original medicine butyphthalide, the organic amine ester derivative of 2-(α-hydroxypentyl) benzoic acid or the pharmaceutically acceptable salt thereof has in vivo a better bioavailability, a greater brain aggregation concentration and a more excellent treatment effect, and has a larger potential in the application in the preparation of a drug for preventing and/or treating heart and cerebral ischemic diseases, a drug for preventing and/or treating heart and cerebral artery occlusion diseases, an anti-parkinsonian drug and an anti-senile-dementia drug.

The experiments disclosed by the present disclosure are merely exemplary experiments selected from the large quantity of experiments in the process of the research and development of the present disclosure, and the object of them is merely to explain the druggability, the safety and the effectiveness of the compounds of the present disclosure.

DETAILED DESCRIPTION

The present disclosure will be further explained below by referring to the description of the particular embodiments, but the particular embodiments are not intended to limit the present disclosure. A person skilled in the art can make various modifications or improvements based on the basic idea of the present disclosure, and those modifications or improvements fall within the scope of the present disclosure without departing from the basic idea of the present disclosure.

Example 1. The Synthesis of 2-(1-acetoxylpentyl)benzoic Acid (the Compound 4)

1.24 g (6.5 mmol) of butyphthalide is dissolved in 10 mL of methanol, added 10 mL of a 2 mol·L$^{-1}$ sodium hydroxide solution, and refluxed for 0.5 h. The methanol is removed by reduced-pressure evaporation, 10 mL of distilled water is added for diluting, cooled to −5° C., and acidified under intense stirring by using 0.6 mol·L$^{-1}$ diluted hydrochloric acid to pH 2-3. The water layer is extracted by using ethyl ether (50 mL×3), the ethyl ether solution is diluted by using 200 mL of dichloromethane, sequentially added 2.7 mL (19.6 mmol) of triethylamine and 0.5 g of 4-dimethylaminopyridine (DMAP), added dropwisely at −5° C. 1.5 mL (19.6 mmol) of acetyl chloride, and, when the dropping has ended, stirred at −5° C. for reaction for 5 h. 10 mL of water is added, and stirring is performed at room temperature for 0.5 h. The organic layer is separated, dried by using anhydrous sodium sulfate, and filtered and condensed to obtain a wax-like solid. The solid is recrystallized in n-hexane to obtain a white needle-like crystal.

Example 2. The Synthesis of the Compound DB-1

0.5 g of 2-(1-acetoxylpentyl)benzoic acid is weighed, added 50 mL of dichloromethane, 0.9 g of HATU and 0.6 mL of N,N-dimethylethanolamine, and stirred for reaction overnight. Water is added for extraction three times, and column purification is performed by using dichloromethane/methanol=80:1, to obtain a white solid. An anhydrous ethanol-HCl solution is added to form a salt, and ethyl ether is added to form a white precipitate. The white precipitate is filtered and dried, to obtain a hydrochloride product, which is the hydrochloride of the compound DB-1.

$^1$H NMR (400 MHz, D2O) δ 7.88 (dd, J=7.8, 1.3 Hz, 1H), 7.65-7.52 (m, 2H), 7.39 (ddd, J=8.0, 7.0, 1.7 Hz, 1H), 6.30 (dd, J=8.4, 4.8 Hz, 1H), 4.70-4.55 (m, 2H), 3.60 (t, J=5.0 Hz, 2H), 2.94 (s, 6H), 2.04 (s, 3H), 1.79 (dddd, J=18.7, 14.2, 11.1, 5.7 Hz, 2H), 1.38-1.21 (m, 4H), 0.79 (t, J=7.1 Hz, 3H).

Example 3. The Synthesis of the Compound DB-2

0.5 g of 2-(1-acetoxylpentyl)benzoic acid is weighed, added 50 mL of dichloromethane, 0.9 g of HATU and 0.8 mL of 1-(2-ethoxy)piperidine, and stirred for reaction overnight. Water is added for extraction three times, and column purification is performed by using dichloromethane/methanol=80:1, to obtain a white solid. An anhydrous ethanol-HCl solution is added to form a salt, and ethyl ether is added to form a white precipitate. The white precipitate is filtered and dried, to obtain a hydrochloride product, which is the hydrochloride of the compound DB-2.

Example 4. Investigation of the Solubilities of Butyphthalide (NBP), DB-1 Hydrochloride or DB-2 Hydrochloride in pH 1.0, 4.5 and 6.8 and Water 1. The experiment process A pH 1.0 HCl solution, a pH 4.5 acetate buffer solution, a pH 6.8 phosphate buffer solution and 5 mL of ultrapure water are added into graduated test tubes having stoppers. Small amounts of the test samples (butyphthalide (NBP), DB-1 hydrochloride or DB-2 hydrochloride) are weighed and added in batches. After each batch of the adding, intense shaking is performed for 30 seconds (ultrasound is prohibited), the dissolving is observed at any time, and when the test samples are add so that turbid insoluble particles or liquid drops can be seen, finally proper amounts of the test samples are added. The system is placed into a 37° C. water bath and vibrated overnight, to form a supersaturated solution. The supersaturated solution is centrifuged or filtered (the adsorption should be noticed), and 100 μL is fed into HPLC to measure the concentrations of the tested medicines.

2. The Experiment Result and Analysis

Figure 1:
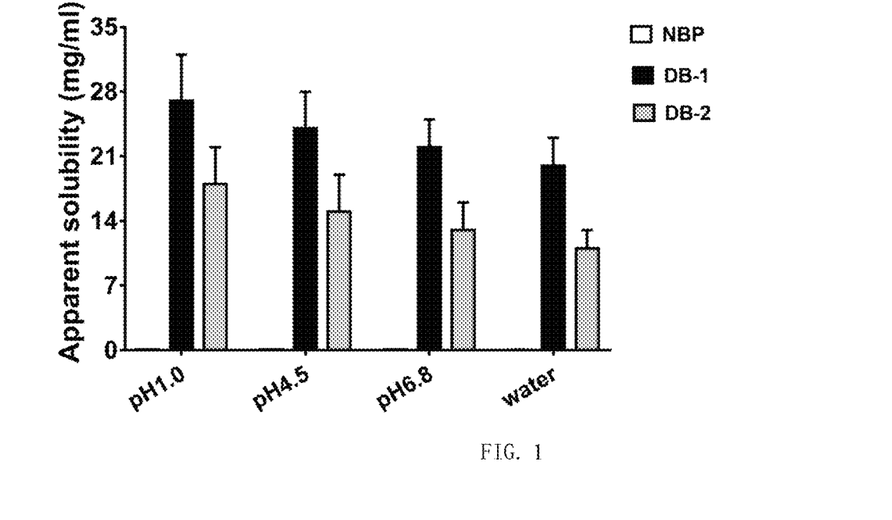
FIG. 1 shows the solubilities of NBP, DB-1 or DB-2 in buffer solutions of different pH values and in pure water, with the unit of mg/mL.

The result of the measurements on the solubilities of butyphthalide (NBP), DB-1 hydrochloride or DB-2 hydrochloride in the buffer solutions of different pH values and in pure water is shown in FIG. 1. Butyphthalide (NBP) belongs to the type of simple phthalides, and is an oily liquid at normal temperature. Therefore, its solubility in pure water is extremely low, and it has an apparent solubility of 0.0734±0.0123 mg/mL, and is an insoluble medicine. Because pH does not highly influence the structure of isobenzofuranone, the difference between the solubilities of butyphthalide (NBP) in the buffer salt solutions of different pH values and the solubility in pure water is not obvious, and the value of the difference is extremely low. The apparent solubility of DB-1 hydrochloride in pure water is 20.017±2.978 mg/mL, and the apparent solubility of DB-2 hydrochloride in pure water is 11.653±1.894 mg/mL. Therefore, both of them are soluble medicines. Because both of DB-1 hydrochloride and DB-2 hydrochloride contain the structure of an organic amine, pH greatly influences their solubilities. Their solubilities are highest in the pH 1.0 HCl solution, and as the pH increases, the solubilities gradually decrease. Because the organic amine in DB-2 hydrochloride is of a cyclic structure, as compared with DB-1 hydrochloride, its solubility is smaller. By the modification of the organic-amine modifications, the solubilities of DB-1 hydrochloride and DB-2 hydrochloride in pure water are greatly increased, which lays the foundation for subsequent studies, and provides more possibility for the studies on the drugability of DB-1 hydrochloride or DB-2 hydrochloride.

Example 5. The Investigation on the Hygroscopicities of the Sodium Salt of 2-(α-hydroxypentyl)benzoic acid (NBP), DB-1 hydrochloride and DB-2 hydrochloride 1. The Experiment Process Three samples of each of the sodium salt of 2-(α-hydroxypentyl)benzoic acid, DB-1 and DB-2 are precisely weighed with approximately 0.2 g for each sample, and placed into weighing bottles, and the total masses of each of the samples and its weighing bottle are weighed and recorded. Then the weighing bottles are placed in a closed environment at 25° C. and at a constant humidity with the relative humidity of 75%, their masses are weighed at 6 h, 12 h, 24 h, 48 h, 96 h and 120 h, and the moisture absorption/weight gaining percentages are calculated. The moisture absorption/weight gaining percentages are calculated by using the formula as follows: moisture absorption/weight gaining percentage (%)=(sample mass after dilution—sample mass before dilution)/sample mass before dilution*100%.

2. The Experiment Result and Analysis

The result of the measurements on the moisture absorption/weight gaining percentages of the sodium salt of 2-(α-hydroxypentyl)benzoic acid (NBP), DB-1 hydrochloride and DB-2 hydrochloride is shown in Table 1. The sodium salt of 2-(α-hydroxypentyl)benzoic acid (NBP) has a high hygroscopicity in the closed environment at 25° C. and at a constant humidity with the relative humidity of 75%, and at 120 h, its moisture absorption/weight gaining percentage is 2.49±0.25%. However, at 120 h, the moisture absorption/weight gaining percentages of DB-1 hydrochloride and DB-2 hydrochloride are 1.03±0.07% and 0.76±0.06% respectively, which demonstrates greatly improved hygroscopicities. In the processes of drug preparation and storage, hygroscopicity is a property of vital importance, and it directly affects the stability of drugs, and even affects the efficacy of drugs. As compared with the sodium salt of 2-(α-hydroxypentyl)benzoic acid (NBP), the hygroscopicities of DB-1 hydrochloride and DB-2 hydrochloride are greatly improved, which lays the foundation for subsequent studies, and provides more possibility for the studies on the druggability of DB-1 hydrochloride or DB-2 hydrochloride. The following Table 1 shows the result of the measurements on the moisture absorption/weight gaining percentages of the sodium salt of 2-(α-hydroxypentyl)benzoic acid (NBP), DB-1 and DB-2.

TABLE 1

| Time (h) | 6 | 12 | 24 | 48 | 96 | 120 |
|---|---|---|---|---|---|---|
| NBP | 0.67 ± 0.12 | 1.43 ± 0.34 | 1.82 ± 0.26 | 2.35 ± 0.31 | 2.44 ± 0.27 | 2.49 ± 0.25 |
| DB-1 | 0.42 ± 0.09 | 0.65 ± 0.16 | 0.88 ± 0.13 | 0.93 ± 0.09 | 0.97 ± 0.11 | 1.03 ± 0.07 |
| DB-2 | 0.38 ± 0.08 | 0.54 ± 0.12 | 0.65 ± 0.08 | 0.71 ± 0.12 | 0.72 ± 0.08 | 0.76 ± 0.06 |

Example 6. The Preparation of Injections Containing DB-1 or DB-2

1 g of the compound DB-1 or DB-2 is precisely weighed, and a proper amount of water for injection is added. The pH is adjusted to 6.5-7.2, and water for injection is added to fix the volume at 1000 mL. The system is added activated carbon to adsorb heat source, filtered by using a 0.22 m microfiltration membrane, and aseptically filled into a sterile ampoule bottle to prepare an injection that can be used for intravenous injection.

Example 7. The Experiments on the Pharmacokinetics and the In-Vivo Distributions in the Mice 1. Animal Grouping and Dosage Regimen 90 Kunming mice (male; 20±2 g) are randomly grouped into three groups, with 30 mice in each of the groups. The first group is the butyphthalide group, is divided into 6 subgroups (5 mice in each of the subgroups), and is administered with butyphthalide by 10 mg/kg. The secondary group is the DB-1 group, is divided into 6 subgroups (5 mice in each of the subgroups), and is administered with DB-1 of the equal moles to the butyphthalide. The third group is the DB-2 group, is divided into 6 subgroups (5 mice in each of the subgroups), and is administered with DB-2 of the equal moles to the butyphthalide. Before the experiment the mice are fasted and are free to drink water. At 5 min, 15 min, 30 min, 1 h, 2 h and 4 h, all of the groups are taken blood at the orbit and then executed, and the hearts, livers, spleens, lungs, kidneys and brains of the mice are immediately separated, washed by using normal saline, dried by using filter paper, weighed, added normal saline of a certain multiple, homogenized, placed into a −40° C. refrigerator, and refrigerated for use. The whole blood is centrifuged at 4500 r/min for 5 min, and the plasma is sucked and placed into a −40° C. refrigerator for use. The stored tissue homogenates are thawed, and 0.1 mL of each of the tissue homogenates is placed into a 0.5 mL EP tube, and added 0.2 mL of acetonitrile protein for precipitation. The precipitate is treated by vortex shocking for 5 minutes, and centrifuged at 10000 rpm for 10 min, and 1 L of the supernatant is fed into an LC-MS/MS system, for measuring the concentrations of the tested medicines.

Figure 2:
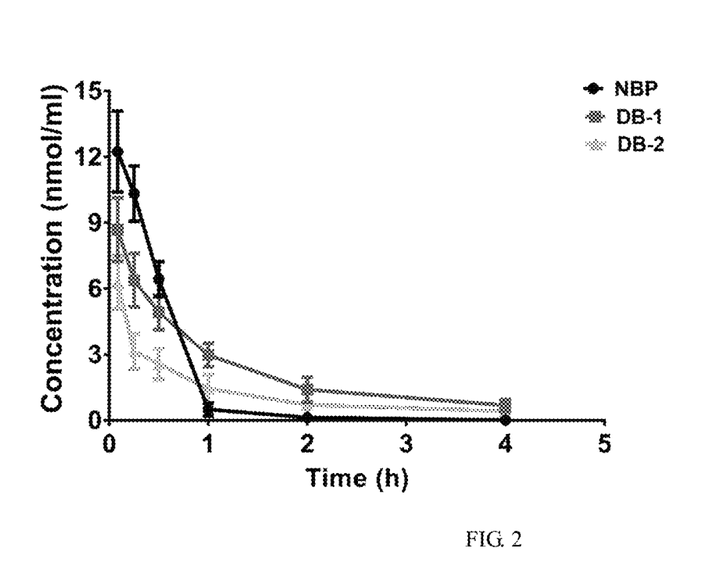
FIG. 2 shows the curves of the average blood concentration versus time of NBP, DB-1 and DB-2, wherein n=5.

2. The Experiment Results and Analysis 2.1 the Result of the Measurements on the Pharmacokinetics of the Mice The curves of the average blood concentration versus time of the sodium salt of 2-(α-hydroxypentyl)benzoic acid (NBP), DB-1 hydrochloride and DB-2 hydrochloride are shown in FIG. 2. The result indicates that the sodium salt of 2-(α-hydroxypentyl)benzoic acid (NBP) is ingested quickly in the mice in vivo. At 5 min after the intravenous administration, their blood concentrations are 12.243±1.847 nmol/mL, and, at 1 h after the administration, quickly decrease to 0.547±0.289 nmol/mL, wherein the ingestion process presents the characteristic of first-order kinetics. At 0.083 h, 0.25 h and 0.5 h after the administration, the blood concentrations of DB-2 hydrochloride are the lowest; at 5 min after the intravenous administration, its blood concentrations are 6.294±1.203 nmol/mL; and, at 1 h after the administration, the concentrations quickly decrease to 1.452±0.657 nmol/mL. However, its metabolism speed is less than that of the sodium salt of 2-(α-hydroxypentyl)benzoic acid (NBP). Throughout the measurement process, the blood concentrations of DB-1 hydrochloride are always greater than those of DB-2 hydrochloride; at 5 min after the intravenous administration, its blood concentrations are 8.684±1.482 nmol/mL; and, at 1 h after the administration, the concentrations quickly decrease to 2.981±0.534 nmol/mL. As compared with the sodium salt of 2-(α-hydroxypentyl)benzoic acid (NBP), the in-vivo ingestion speeds of DB-1 hydrochloride and DB-2 hydrochloride are reduced, which might be because of the influences by the physicochemical properties of DB-1 hydrochloride and DB-2 hydrochloride such as the solubilities, the lipo-hydro partition coefficients and the dissociation constants, and might be related to the in-vivo metabolism process.

Figure 3:
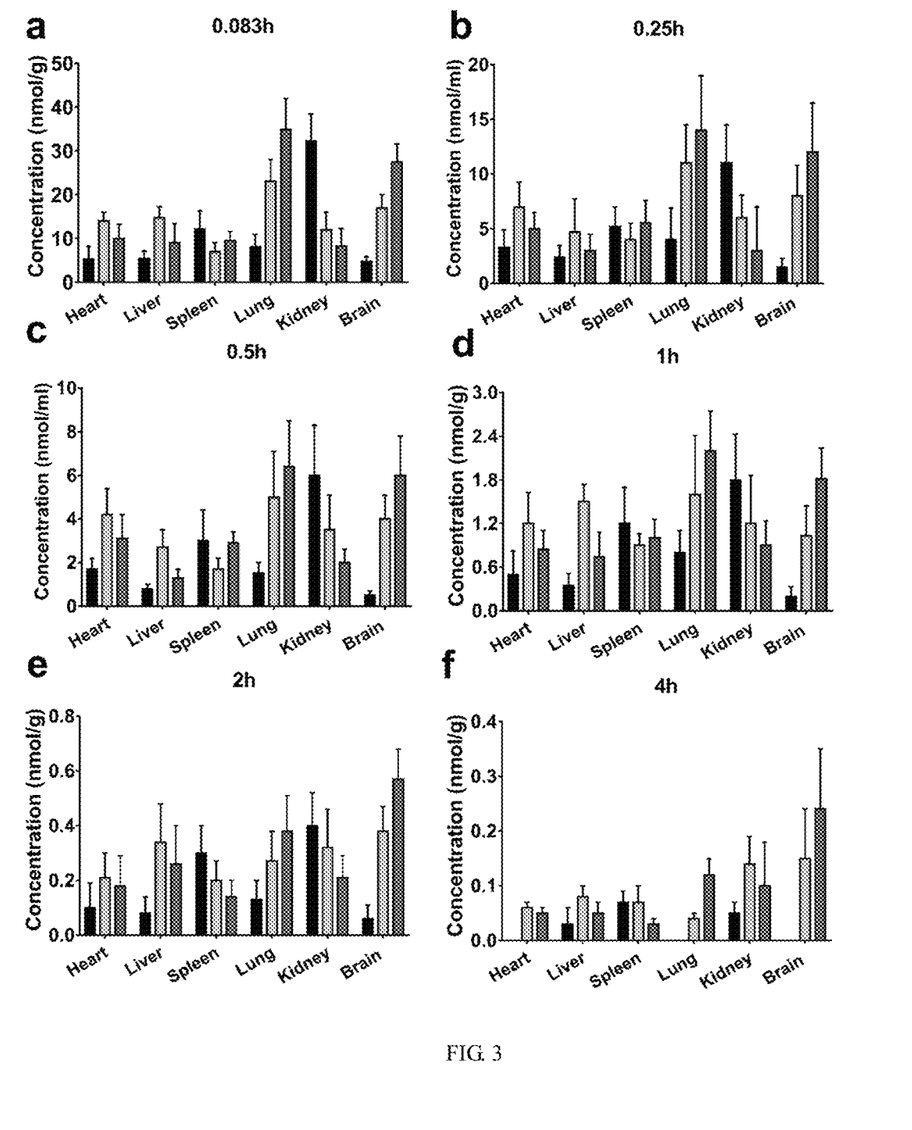
FIG. 3 shows the profiles of the tissue distributions at different administration time points of NBP, DB-1 and DB-2, wherein n=5.

2.2 the Result of the Experimental Measurements on the In-Vivo Distributions in the Mice The profiles of the tissue distributions at different administration time points of the sodium salt of 2-(α-hydroxypentyl)benzoic acid (NBP), DB-1 hydrochloride and DB-2 hydrochloride are shown in FIG. 3. The result indicates that the sodium salt of 2-(α-hydroxypentyl)benzoic acid (NBP) can permeate the blood-brain barrier and enter the brain; the concentrations in the kidney are greater, which might be because part of the medicine is metabolized via the kidney; and the distributions among the other tissues are relatively even. The sodium salt of 2-(α-hydroxypentyl)benzoic acid (NBP) is ingested quickly in vivo. At 1 h after the administration, the concentrations of it in all of the tissues are low, and at 4 h, the contents in the heart, the lung and the brain are too low to be detected, which is consistent with the result of the in-vivo pharmacokinetics experimentation of the sodium salt of 2-(α-hydroxypentyl)benzoic acid (NBP). DB-1 hydrochloride and DB-2 hydrochloride can also permeate the blood-brain barrier and enter the brain, and at all of the detection time points the contents in the brain of them are significant greater than that of the sodium salt of 2-(α-hydroxypentyl)benzoic acid (NBP), which indicates that DB-1 hydrochloride and DB-2 hydrochloride have the potential of serving as brain targeted medicines. Moreover, the contents in the lung of DB-1 hydrochloride and DB-2 hydrochloride are also greater, which might be related to the modifying organic amines in their structures. However, the contents in the kidney are smaller, so it is speculated that the speeds of ingestion via the kidney of DB-1 hydrochloride and DB-2 hydrochloride are less than that of the sodium salt of 2-(α-hydroxypentyl)benzoic acid (NBP). As compared with DB-1 hydrochloride, the accumulated concentration in the brain of DB-2 hydrochloride is greater, which, as the inventors can assure, is related to the structure of its side chain.

2.3 the Assessment on the Targeting Ability

The pharmacokinetic parameters are calculated by using the DAS3.2.5 software. Regarding the quantitative assessment on the brain targeting ability of the sodium salt of 2-(α-hydroxypentyl)benzoic acid (NBP), DB-1 hydrochloride and DB-2 hydrochloride, the following parameters are employed: relative uptake ratio ($Re_{brain}$), peak concentration ratio ($Ce_{brain}$) and drug targeting index ($DTI_{brain}$), the calculating formulas of which are respectively:

$$Re_{(brain, DB-1)} = (AUC_{brain})_{DB-1} / (AUC_{brain})_{NBP}$$

$$Ce_{DB-1} = (Cmax_{,brain})_{DB-1} / (Cmax_{,brain})_{NBP}$$

$$DTI_{DB-1} = (AUC_{brain}/AUC_{plasma})_{DB-1} / (AUC_{brain}/AUC_{plasma})_{NBP}$$

$$Re_{(brain, DB-2)} = (AUC_{brain})_{DB-2} / (AUC_{brain})_{NBP}$$

$$Ce_{DB-2} = (Cmax_{,brain})_{DB-2} / (Cmax_{,brain})_{NBP}$$

$$DTI_{DB-2} = (AUC_{brain}/AUC_{plasma})_{DB-2} / (AUC_{brain}/AUC_{plasma})_{NBP}$$

wherein the $Re_{(brain, DB-1)}$ and the $Re_{(brain, DB-2)}$ are used to assess whether the medicines have a brain targeting ability, wherein a value greater than 1 indicates that the medicines have a brain targeting ability, a greater value of the Re indicates a better brain targeting ability, and a value equal to or less than 1 indicates that they do not have a brain targeting ability; the Ce DB-1 and the Ce DB-2 represent the effects of brain target distribution of the medicines, wherein if the value of the Ce is greater, the effect of the brain target distribution is more obvious; and the DTI is the optimal parameter for assessing the target effectiveness of the medicines. The calculation results of the parameters can be seen in Table 2. Regarding DB-1, the brain relative uptake ratio Re is 3.64, the peak concentration ratio Ce is 2.93, and the drug targeting index DTI is 12.45. Regarding DB-2, the brain relative uptake ratio Re is 4.27, the peak concentration ratio Ce is 3.19, and the drug targeting index DTI is 18.08.

It can be known from the results that, after the sodium salt of 2-(α-hydroxypentyl)benzoic acid (NBP) is modified by the organic amines, the distribution in the plasma is reduced, and the distribution in the brain is significantly increased, which indicates an significant targeting ability (p<0.05). The following Table 2 shows the results of the calculation of the brain targeting parameters of the sodium salt of 2-(α-hydroxypentyl)benzoic acid (NBP), DB-1 and DB-2

TABLE 2

| Parameter | NBP | DB-1 | DB-2 |
|---|---|---|---|
| $Re_{brain}$ | / | 3.64 | 4.27 |
| $Ce_{brain}$ | / | 2.93 | 3.19 |
| DTI | / | 12.45 | 18.08 |

3. Conclusion

The study results of the experiments of the in-vivo pharmacokinetics and the in-vivo distributions in the mice of the sodium salt of 2-(α-hydroxypentyl)benzoic acid (NBP), DB-1 and DB-2 indicate that, after the sodium salt of 2-(α-hydroxypentyl)benzoic acid (NBP) is modified by the organic amines, the in-vivo metabolism dynamics and tissue distributions of the compounds DB-1 and DB-2 may be changed, and the distribution concentrations in the brain of the compounds DB-1 and DB-2 are obviously increased, which indicates that the goal of brain targeted administration has been reached. The property of the brain targeting of the compounds DB-1 and DB-2, which might be because of the influences by the physicochemical properties of DB-1 hydrochloride and DB-2 hydrochloride such as the solubilities, the lipo-hydro partition coefficients and the dissociation constants, and might be related to the in-vivo metabolism process.

The "one embodiment", "an embodiment" or "one or more embodiments" as used herein means that particular features, structures or characteristics described with reference to an embodiment are included in at least one embodiment of the present disclosure. Moreover, it should be noted that here an example using the wording "in an embodiment" does not necessarily refer to the same one embodiment.

The description provided herein describes many concrete details. However, it can be understood that the embodiments of the present disclosure may be implemented without those concrete details. In some of the embodiments, well-known processes, structures and techniques are not described in detail, so as not to affect the understanding of the description.

Finally, it should be noted that the above embodiments are merely intended to explain the technical solutions of the present disclosure, and not to limit them. Although the present disclosure is explained in detail by referring to the above embodiments, a person skilled in the art should understand that he can still modify the technical solutions set forth by the above embodiments, or make equivalent substitutions to part of the technical features of them. However, those modifications or substitutions do not make the essence of the corresponding technical solutions depart from the spirit and scope of the technical solutions of the embodiments of the present disclosure.

What is claimed is:

1. An organic amine ester derivative of 2-(α-hydroxypentyl)benzoic acid, wherein the organic amine ester derivative of 2-(α-hydroxypentyl)benzoic acid is a compound having the following general formula I, or the organic amine ester derivative of 2-(α-hydroxypentyl)benzoic acid is a pharma- ceutically acceptable salt formed by a compound having the following general formula I and an inorganic acid or organic acid:

(I)

wherein, in the general formula I, R₁ represents hydrogen atom or C1-C10 alkyl, wherein the C1-C10 alkyl is substituted with acyl or acyloxy; and X represents a substituent wherein R₂ is C1-C10 alkylene or C3-C7 cycloalkylene, and R₃ and R₄ are independently selected from hydrogen atom, C1-C10 alkyl and C3-C7 cycloalkyl; or, X represents a substituent wherein n is an integer selected from an interval [0, 10] and R₅ represents a 5-15-membered heterocycle or substituted heterocycle containing one or two nitrogen atoms.

2. The organic amine ester derivative of 2-(α-hydroxypentyl)benzoic acid according to claim 1, wherein the organic amine ester derivative of 2-(α-hydroxypentyl)benzoic acid is a compound having the following general formula II, or the organic amine ester derivative of 2-(α-hydroxypentyl)benzoic acid is a pharmaceutically acceptable salt formed by a compound having the following general formula II and an inorganic acid or organic acid;

(II)

wherein
X represents a substituent wherein R₂ is C1-C10 alkylene or C3-C7 cycloalkylene, and R₃ and R₄ are independently selected from hydrogen atom, C1-C10 alkyl and C3-C7 cycloalkyl; or,

X represents a substituent wherein n=2 and R₅ represents any one of

3. The organic amine ester derivative of 2-(α-hydroxypentyl)benzoic acid according to claim 2, wherein the organic amine ester derivative of 2-(α-hydroxypentyl)benzoic acid is a compound having the following structure, or the organic amine ester derivative of 2-(α-hydroxypentyl)benzoic acid is a pharmaceutically acceptable salt formed by a compound having the following structure and an inorganic acid or organic acid:

DB-2

4. The organic amine ester derivative of 2-(α-hydroxypentyl)benzoic acid according to claim 1, wherein
the inorganic acid is hydrochloric acid, hydrobromic acid, sulfuric acid, or phosphoric acid; and
the organic acid is acetic acid, trifluoroacetic acid, lactic acid, pyruvic acid, propanedioic acid, succinic acid, glutaric acid, fumaric acid, tartaric acid, maleic acid, citric acid, ascorbic acid, oxalic acid, camphoric acid, gluconic acid, glucuronic acid, pamoic acid, methanesulfonic acid, ethanesulfonic acid, aminosulfonic acid, or p-toluenesulfonic acid.

5. A method for preparing the organic amine ester derivative of 2-(α-hydroxypentyl)benzoic acid according to claim 1, wherein the method for preparing the compound having the general formula I comprises:

performing an acylation reaction between a compound 2-(α-hydroxypentyl)benzoic acid having the following structure 1 and an acylating reagent having the following general formula III, to obtain an intermediate compound having the following general formula IV; and performing an esterification reaction between the intermediate compound and an esterifying reagent having the following general formula V, to obtain the compound having the general formula I

1

III

IV

X—OH;

V wherein R$_1$ in the general formula III of the acylating reagent represents hydrogen atom or C1-C10 alkyl, wherein the C1-C10 alkyl is substituted with acyl or acyloxy; and X in the general formula V of the esterifying reagent represents a substituent wherein R$_2$ is C1-C$_{10}$ alkylene or C3-C7 cycloalkylene, and R$_3$ and R$_4$ are independently selected from hydrogen atom, C1-C10 alkyl and C3-C7 cycloalkyl; or, X represents a substituent —(CH$_2$)$_n$—R$_5$, wherein n is an integer selected from an interval [0, 10] and R$_5$ represents a 5-15-membered heterocycle or substituted heterocycle containing one or two nitrogen atoms.

6. The method according to claim 5, wherein
R$_1$ in the general formula III of the acylating reagent is acetyl; and
X in the general formula V of the esterifying reagent represents a substituent wherein R$_2$ is C1-C10 alkylene or C3-C7 cycloalkylene, and R$_3$ and R$_4$ are independently selected from hydrogen atom, C1-C10 alkyl and C3-C7 cycloalkyl; or,

X represents a substituent

—(CH$_2$)$_n$—R$_5$, wherein n=2 and R$_5$ represents any one of

7. The method according to claim 6, wherein the esterifying reagent is N,N-dimethylethanolamine, which means that X in the general formula V of the esterifying reagent represents a substituent wherein R$_2$ is ethylidene, R$_3$ is methyl and R$_4$ is methyl; and
the step of performing an esterification reaction between the intermediate compound and an esterifying reagent having the following general formula V, to obtain the compound having the general formula I comprises:

performing an esterification reaction between the intermediate compound and N,N-dimethylethanolamine, to obtain the compound having the following structure;

DB-1

8. The method according to claim 6, wherein the esterifying reagent is 1-(2-ethoxy)piperidine, which means that X in the general formula V of the esterifying reagent represents a substituent wherein n=2 and $R_5$ represents and the step of performing an esterification reaction between the intermediate compound and an esterifying reagent having the following general formula V, to obtain the compound having the general formula I comprises:
performing an esterification reaction between the intermediate compound and 1-(2-ethoxy)piperidine, to obtain the compound having the following structure;

DB-2

9. The method according to claim 5, wherein the method further comprises:
preparation of the salt: adding the inorganic acid or organic acid into the obtained compound having the general formula I to perform the reaction, to obtain the pharmaceutically acceptable salt formed by the compound having the general formula I and the inorganic acid or organic acid.

10. The method according to claim 9, wherein
the inorganic acid is hydrochloric acid, hydrobromic acid, sulfuric acid, or phosphoric acid; and
the organic acid is acetic acid, trifluoroacetic acid, lactic acid, pyruvic acid, propanedioic acid, succinic acid, glutaric acid, fumaric acid, tartaric acid, maleic acid, citric acid, ascorbic acid, oxalic acid, camphoric acid, gluconic acid, glucuronic acid, pamoic acid, methanesulfonic acid, ethanesulfonic acid, aminosulfonic acid, or p-toluenesulfonic acid.

11. A pharmaceutically acceptable formulation prepared from the organic amine ester derivative of 2-(α-hydroxypentyl)benzoic acid according claim 1, wherein the formulation is a solid formulation, a semi-solid formulation, or a liquid formulation.

12. The formulation according to claim 11, wherein the solid formulation is a common tablet, a dispersible tablet, a sustained release tablet, a soft capsule, a hard capsule, a granula, a pulvis or a suppository;

the semi-solid formulation is an ointment, a paste, or a gel; and
the liquid formulation is an injection, a drop, a solution, an emulsion, or a suspension, wherein the injection consists of 1 g of DB-1 and 1000 mL of water.

13. A method of treating a subject with heart ischemic disease, cerebral ischemic disease, heart artery occlusion, or cerebral artery occlusion, comprising administering to the subject the formulation according to claim 12.

14. An organic amine ester derivative of 2-(α-hydroxypentyl)benzoic acid, wherein the organic amine ester derivative of 2-(α-hydroxypentyl)benzoic acid is a compound having the following general formula DB-1, or the organic amine ester derivative of 2-(α-hydroxypentyl)benzoic acid is a pharmaceutically acceptable salt formed by a compound having the following general formula DB-1 and an inorganic acid or organic acid:

DB-1

15. The organic amine ester derivative of 2-(α-hydroxypentyl)benzoic acid according to claim 1, wherein
the inorganic acid is hydrochloric acid, hydrobromic acid, sulfuric acid, or phosphoric acid; and
the organic acid is maleic acid.

16. A method for preparing the organic amine ester derivative of 2-(α-hydroxypentyl)benzoic acid according to claim 14, wherein the method for preparing the compound having the general formula DB-1 comprises:
performing an acylation reaction between a compound 2-(α-hydroxypentyl)benzoic acid having the following structure 1 and an acylating reagent having the following general formula III, to obtain an intermediate compound having the following general formula IV; and
performing an esterification reaction between the intermediate compound and an esterifying reagent having the following general formula V, to obtain the compound having the general formula I;

-continued

IV

X—OH;
V wherein $R_1$ in the general formula III of the acylating reagent represents $C_2$ acyl; and X in the general formula V of the esterifying reagent represents a substituent wherein $R_2$ is —CH2—CH2—, and $R_3$ and $R_4$ are CH3.

17. The method according to claim 16, wherein the method further comprises:

preparation of the salt: adding the inorganic acid or organic acid into the obtained compound having the general formula DB-1 to perform the reaction, to obtain the pharmaceutically acceptable salt formed by the compound having the general formula DB-1 and the inorganic acid or organic acid.

18. The method according to claim 17, wherein the inorganic acid is hydrochloric acid, hydrobromic acid, sulfuric acid, or phosphoric acid; and the organic acid is maleic acid.

19. A pharmaceutically acceptable formulation prepared from the organic amine ester derivative of 2-(α-hydroxypentyl)benzoic acid according to claim 14, wherein the formulation is an injection consisting of 1 g of DB-1 and 1000 mL of water.

20. A method of treating a subject with heart ischemic disease, cerebral ischemic disease, heart artery occlusion, or cerebral artery occlusion, comprising administering to the subject the formulation according to claim 19.

\* \* \* \* \*